United States Patent [19]

Remy

[11] 4,275,070

[45] Jun. 23, 1981

[54] ANTIPSYCHOTIC PHARMACEUTICAL COMPOSITIONS OF THE LEVOROTATORY ENANTIOMERS OF 3-METHOXYCYPROHEPTADINE AND AN ANALOG THEREOF

[75] Inventor: David C. Remy, North Wales, Pa.

[73] Assignee: Merck & Co., Inc., Rahway, N.J.

[21] Appl. No.: 151,232

[22] Filed: May 19, 1980

Related U.S. Application Data

[62] Division of Ser. No. 40,820, May 21, 1979, abandoned.

[51] Int. Cl.$^3$ .................................... A61K 31/445
[52] U.S. Cl. .................................... 424/267; 546/203; 546/204
[58] Field of Search ................. 424/267; 546/203, 204

[56] References Cited

U.S. PATENT DOCUMENTS

| 3,014,911 | 12/1961 | Remy | 546/203 |
| 4,031,222 | 6/1977 | Remy | 546/203 |
| 4,104,398 | 8/1978 | Remy | 424/267 |
| 4,132,796 | 1/1979 | Remy | 546/204 |

FOREIGN PATENT DOCUMENTS 746508 11/1966 Canada .................................... 546/203

OTHER PUBLICATIONS

Gordon, M. (Editor), Psychopharmacological Agents, vol. 1, Academic Press., N.Y. (1964), pp. 600–603.
Ebnöther, A. et al., Helv. Chim. Acta., 48 1237 (1965).

*Primary Examiner*—Stanley J. Friedman
*Attorney, Agent, or Firm*—William H. Nicholson; Mario A. Monaco

[57] ABSTRACT

The levorotatory enantiomers of 3-methoxy cyproheptadine and a related compound are antipsychotic agents.

4 Claims, No Drawings

ANTIPSYCHOTIC PHARMACEUTICAL COMPOSITIONS OF THE LEVOROTATORY ENANTIOMERS OF 3-METHOXYCYPROHEPTADINE AND AN ANALOG THEREOF

This is a division of application Ser. No. 040,820 filed May 21, 1979, now abandoned.

BACKGROUND OF THE INVENTION

This invention is concerned with pharmaceutical compositions comprising the levorotatory enantiomers of 3-methoxycyproheptadine and a related compound and their use as antipsychotic agents. It is also concerned with the optically active enantiomers of 1-cyclopropylmethyl-4-(3-methoxy-5H-dibenzo[a,d]cyclohepten-5-ylidene)piperidine, as a novel compound.

The levorotatory enantiomer of 3-methoxycyproheptadine is known as an antiserotonin agent in U.S. Pat. No. 4,104,398.

Now with this invention there are provided novel pharmaceutical compositions comprising levorotatory 3-methoxycyproheptadine or an analog thereof as active ingredient, which are useful as antipsychotic agents.

There is also provided a novel method of treating psychoses with these novel pharmaceutical compositions.

There are also provided certain novel compounds within the class of 3-methoxycyproheptadines and analogs thereof and novel processes for synthesizing these novel compounds.

DETAILED DESCRIPTION OF THE INVENTION

The novel compounds of this invention are the levorotatory and dextrorotatory enantiomers of 1-cyclopropylmethyl-4-(3-methoxy-5H-dibenzo[a,d]-cyclohepten-5-ylidene)piperidine, having structural formula:

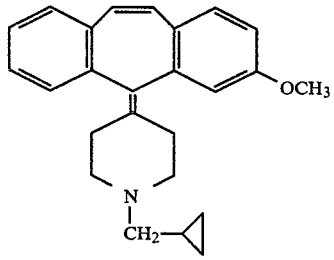

I or a pharmaceutically acceptable salt thereof.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, pamoate, citrate, napsylate, pyruvate, isethionate, maleate, fumarate, or the like.

The salts are prepared by dissolving approximately equimolecular amounts of the free base compound and the desired acid in a solvent followed by crystallization of the salt product.

The novel process for the preparation of the compounds of this invention comprises dehydration of 1-cyclopropylmethyl-4-(3-methoxy-5-hydroxy-5H-dibenzo[a,d]cyclohepten-5-yl)piperidine with a dehydrating agent such as trifluoroacetic acid/trifluoroacetic anhydride at reflux temperature, to form a racemic mixture of the novel compounds of this invention. The racemic mixture is then resolved by formation of diastereomeric salts with it and an optically active acid such as di-p-toluoyl-d-tartaric acid in a solvent such as ethanol followed by separation of the diastereomeric pair of salts such as by fractional crystallization followed by separate treatment of each salt with an alkali such as an alkali metal hydroxide, bicarbonate or carbonate, especially sodium bicarbonate or carbonate to liberate the free (+)— and (−)— enantiomers. The levorotatory isomer is further resolved via recrystallization from a solvent such as acetonitrile.

The optically enriched dextrorotatory compound obtained as described above can be racemized by heating a solution of it in an inert solvent until a sample fails to show optical activity. It is convenient to reflux a toluene solution for about 10–50 hours. In this manner, additional quantities of the racemic compound can be obtained from which additional levorotatory material can be isolated by the above described resolution.

Experimental details for preparation of the novel (−) and (+)-1-cyclopropylmethyl- compounds can be obtained from U.S. Pat. No. 4,104,398, Examples 1 and 2 which describe the synthesis of the corresponding (−) and (+)-1-methyl- compounds respectively.

The compounds useful in the novel method of treatment and novel pharmaceutical formulations of this invention have structural formula:

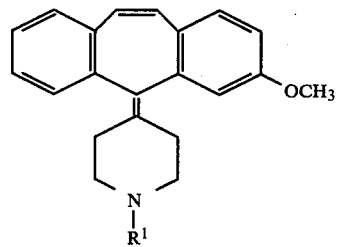

or a pharmaceutically acceptable salt thereof, wherein $R^1$ is methyl or cyclopropylmethyl.

The pharmaceutically acceptable salts contemplated for this purpose are the same salts discussed herein in connection with the novel compounds.

As pointed out by Ebnother et al., Helv. Chim. Acta, 48, 1237–1249 (1965) these compounds exist as levorotatory and dextrorotatory optical enantiomers. All of the antipsychotic activity resides in the levorotatory enantiomers, but the racemic mixtures of the levo- and dextrorotatory enantiomers, the mixture from which the levorotatory enantiomers are obtained are still potent antipsychotic agents and are useful in the novel method of treatment and novel pharmaceutical formulations of this invention. Thus there is contemplated for use in the novel method of treatment and pharmaceutical formulations:

(1) racemic mixtures of levo- and dextrorotatory enantiomers, herein after referred to as "racemic compounds;" and (2) any mixtures optically enriched in the levorotatory sense or pure levorotatory enantiomers, hereinafter referred to as "levorotatory compounds."

The novel method of treatment of this invention comprises the administration of an antipsychotically effective amount of one of the racemic or levorotatory compounds or a pharmaceutically acceptable salt thereof to a psychotic patient. The route of administration can be oral, rectal, intravenous, intramuscular, or subcutaneous. Doses of 0.1 to 20 mg/kg/day and preferably of 0.5 to 10 mg/kg/day of active ingredient are adequate, and if preferred, it can be administered in divided doses given two to four times daily.

It is to be noted that the precise unit dosage form and dosage level depend upon the case history of the individual being treated and, consequently, are left to the discretion of the therapist.

Pharmaceutical compositions comprising a compound useful in the novel method of treatment as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg, and preferably from 5 to 250 mg.

Pharmacology

Antiavoidance Activity in Squirrel Monkeys

Methods:

Squirrel monkeys (*Saimiri sciureus*) of both sexes were trained to press a lever in order to avoid an electric shock. The animals were trained and tested while restrained in a chair in an isolation chamber. The electric shock (600 V a.c., 2 mA, 1 second) was given via leads placed on the seat of the chair and a ring around the animal's neck. Background noise was supplied with a Grason Stadler Noise Generator. A modified Sidman avoidance schedule (RS-36; SS-36) was used, programming 36 seconds of shock-free time after each lever press (avoidance response). A lever press made during a shock (escape response) immediately terminated the shock, resetting the shock-shock interval timer to 36 seconds. The avoidance schedule also contained an "alarm" system to shut off the schedule for 30 minutes, if an animal received 10 consecutive shocks without a lever press. This prevented the animals from receiving an excessive number of shocks. Following the 30-minute alarm period, the schedule resumed again. An animal was assigned the maximum number of shocks (50/30 minutes), if the alarm system was activated during a trial. The test compound was administered by gavage at cumulative doses of 0.33, 1 and 3 mg/kg given at 0, 90 and 180 minutes of the test session.

Results:

(−)-1-methyl-4-(3-methoxy-5H-dibenzo[a,d]cyclohepten-5-ylidene)piperidine caused the monkeys to take a large number of shocks, i.e. avoidance responding was markedly depressed (Table 1). Chlorpromazine, a reference standard, also exhibited a similar action in this test procedure.

TABLE I

| | Antiavoidance Activity in Squirrel Monkey. | | | | | | | | |
|---|---|---|---|---|---|---|---|---|---|
| | Shocks Received/30 Minutes Time (minutes) | | | | | | | | |
| Treatment | 0–30 | 30–60 | 60–90 | 90–120 | 120–150 | 150–180 | 180–210 | 210–240 | 240–270 |
| mg/kg p.o.: | ↑0.33 | | | ↑1.0 | | | ↑3.0 | | |
| Control[a] | 0 | 1 | 0 | 0 | 3 | 0 | 0 | 0 | 0 |
| Test Compound[b] | 1 | 2 | 1 | 2 | 31 | 42 | 37 | 36 | 37 |
| Control[a] | 0 | 1 | 3 | 3 | 3 | 1 | 1 | 2 | 3 |
| Chlorpromazine[b] | 0 | 0 | 0 | 0 | 2 | 2 | 5 | 50 | 50 |

[a]Average of 2 control sessions (one before and one after drug testing) for 3 monkeys.
[b]Average for the same 3 monkeys for one session.

EXAMPLE 1

Pharmaceutical Compositions

A typical tablet containing 100 mg of (−)-1-methyl-4-(3-methoxy-5H-dibenzo[a,d]cyclohepten-5-ylidene)-piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture is then compressed into tablets.

| Tablet Formula | |
|---|---|
| Ingredient | Mg per Tablet |
| (-)-1-methyl-4-(3-methoxy-5H-dibenzpo[a,d]cyclohepten-5-ylidene)piperidine | 100 mg |
| Calcium phosphate | 52 mg |
| Lactose | 60 mg |
| Starch | 10 mg |
| Magnesium stearate | 1 mg |

Similarly tablets containing the other racemic or levorotatory compound active in the novel method of treatment of this invention are prepared by substituting for the (−)-1-methyl-4-(3-methoxy-5H-dibenzo[a,d]cyclohepten-5-ylidene)piperidine a comparable molecular amount of either the racemic or levorotatory 1-cyclopropylmethyl-4-(3-methoxy-5H-dibenzo[a,d]cyclohepten-5-ylidene)-piperidine or a pharmaceutically acceptable salt thereof.

What is claimed is:

1. A method of treating psychoses which comprises the administration to a patient in need of such treatment an effective antipsychotic amount of a racemic or levorotatory compound of formula:

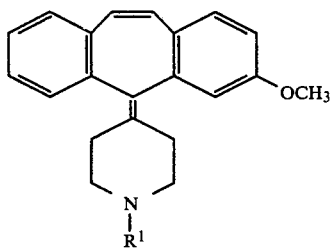

or pharmaceutically acceptable salt thereof wherein $R^1$ is methyl or cyclopropylmethyl.

2. The method of claim 1 wherein the racemic or levorotatory compound is 1-methyl-4-(3-methoxy-5H-dibenzo[a,d]cyclohepten-5-ylidene)-piperidine or pharmaceutically acceptable salt thereof.

3. The method of claim 1 wherein the racemic or levorotatory compound is 1-cyclopropylmethyl-4-(3-methoxy-5H-dibenzo[a,d]cyclohepten-5-ylidene)piperidine or a pharmaceutically acceptable salt thereof.

4. An antipsychotic composition in unit dosage form comprising a pharmaceutical carrier and an effective antipsychotic amount of a racemic or levorotatory compound of formula:

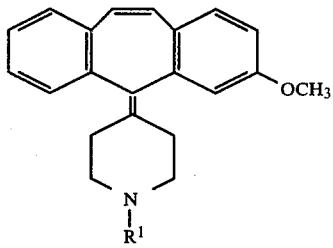

or pharmaceutically acceptable salt thereof, wherein $R^1$ is cyclopropylmethyl.

* * * * *